United States Patent [19]

della Valle

[11] Patent Number: 5,229,373
[45] Date of Patent: Jul. 20, 1993

[54] USE OF EXOGENOUS GANGLIOSIDES AS A PROTECTIVE FACTOR AGAINST TOXICITY BY ANTITUMOR DRUG VINCRISTINE

[75] Inventor: Francesco della Valle, Padova, Italy

[73] Assignee: Fidia S.p.A., Abano Terme, Italy

[21] Appl. No.: 66,248

[22] Filed: Jun. 25, 1987

[30] Foreign Application Priority Data

Jun. 30, 1986 [IT] Italy ............................. 48203 A/86

[51] Int. Cl.$^5$ ............................................. A61K 31/70
[52] U.S. Cl. ....................................... 514/61; 514/54; 514/283; 536/1.11; 536/53; 536/4.1
[58] Field of Search ........................... 514/283, 54, 61; 536/55.1, 53

[56] References Cited

U.S. PATENT DOCUMENTS 4,728,641 3/1988 Jubaro et al. ........................ 514/54

OTHER PUBLICATIONS

Chemical Abstracts 107:126628g.
Chemical Abstracts 108:31499x.
Chemical Abstracts 108:197919j.
Leon et al., Membranes in Growth & Development, 311-320 (1982).
Brown et al., Ann. Rev. Neurosci. 4:17-42 (1981).
Toffano et al., Journal of Neurochemistry 35(4):861-866 (1980).
Aporti et al., Acta Otolaryngol 92:433-437 (1981).
Leon et al., Journal of Neurochemistry, 37(2):350-357 (1981).
Ledeen et al., Journal of Lipid Research, 9, 129-136 (1968).
Svennerholm et al., J. of Biological Chemistry, 248, #2, 740-742 (1973).
Svennerholm, Journal of Neurochemistry, 10, 613-623 (1963).
Fishman et al., Science, vol. 194, 906-915 (1976).
Gorio et al., Gangliosides in Neuro. & Neuromuscular Function, 177-195 (1981).
Gorio et al., Brain Research 197, 236-241 (1980).
Roisen et al., Science, 214, 577-578 (1981).
Hauw et al., C.R. Acad. Sc. Paris, t. 292, pp. 569-571 (1981).
Gorio et al., Birth Defects: Original Article Series, 19, #4, 157-174 (1983).
Norido et al., Experientia 37, pp. 301-302 (1981).
Norido et al., Muscle & Nerve, 5:107-110 (1982).
Maroni et al., Clinical Tosicology, 18(12), 1475-1484 (1981).
Ledeen, TINS, 169-174 (1985).
Hakomori, Ann. Rev. Biochem. 50:733-64 (1981).
Koulakoff et al., Developmental Biology 100, 350-357 (1983).
Willinger et al., Developmental Biology, 74, 101-117 (1980).
Hakomori, Biochimica et Biophysica Acta, 417, 55-89 (1975).
Hakamori, TIBS, Oct. 1984, 453-456.
Holland et al., Cancer Research, 33, 1258-1264 (1973).
Cho et al., Arch. Toxicol. 52:83-90 (1983).
Sato et al., Acta Neuropathol(Berl) 63:150-159 (1984).
McLeod et al., J. Neurol. Neurosurg. Psychiat., 32, 297-304 (1969).
Guiheneuc et al., Journal of Neurological Sciences, 45:355-366 (1980).
Gorio et al., Neuroscience, vol. 8, No. 3, 417-429 (1983).
The Lancet, FEb. 9, 1985, p. 346.
Dantona et al., International Symposium on Peripheral Neuropathies, RICERCA SCIENTIFICA ED EDUCAZIONE PERMANENTE, Suppl. 9, 155-158 (1978).
Azzoni, Il Policlinico-Sez. Medica, vol. 85, No. 4, pp. 1-8 (1978).
Aporti et al., Nuovo Archivio Italiano di Otologia, Rinologia e Laringologia, vol. V, pp. 25-31 (1977).

Primary Examiner—Johnnie R. Brown
Assistant Examiner—Elli Peselev
Attorney, Agent, or Firm—Birch, Stewart, Kolasch & Birch

[57] ABSTRACT

An agent for prevention or prophylaxis of general toxic effects or chronic neurotoxic effects which are caused by the administration of antineoplastic agents, which is to be given to patients prior to administration of said antineoplastic agents and which comprises as an active ingredient a mixture of gangliosides $GM_1$, $GD_{1a}$, $GD_{1b}$ and $GT_{1b}$.

1 Claim, 1 Drawing Sheet

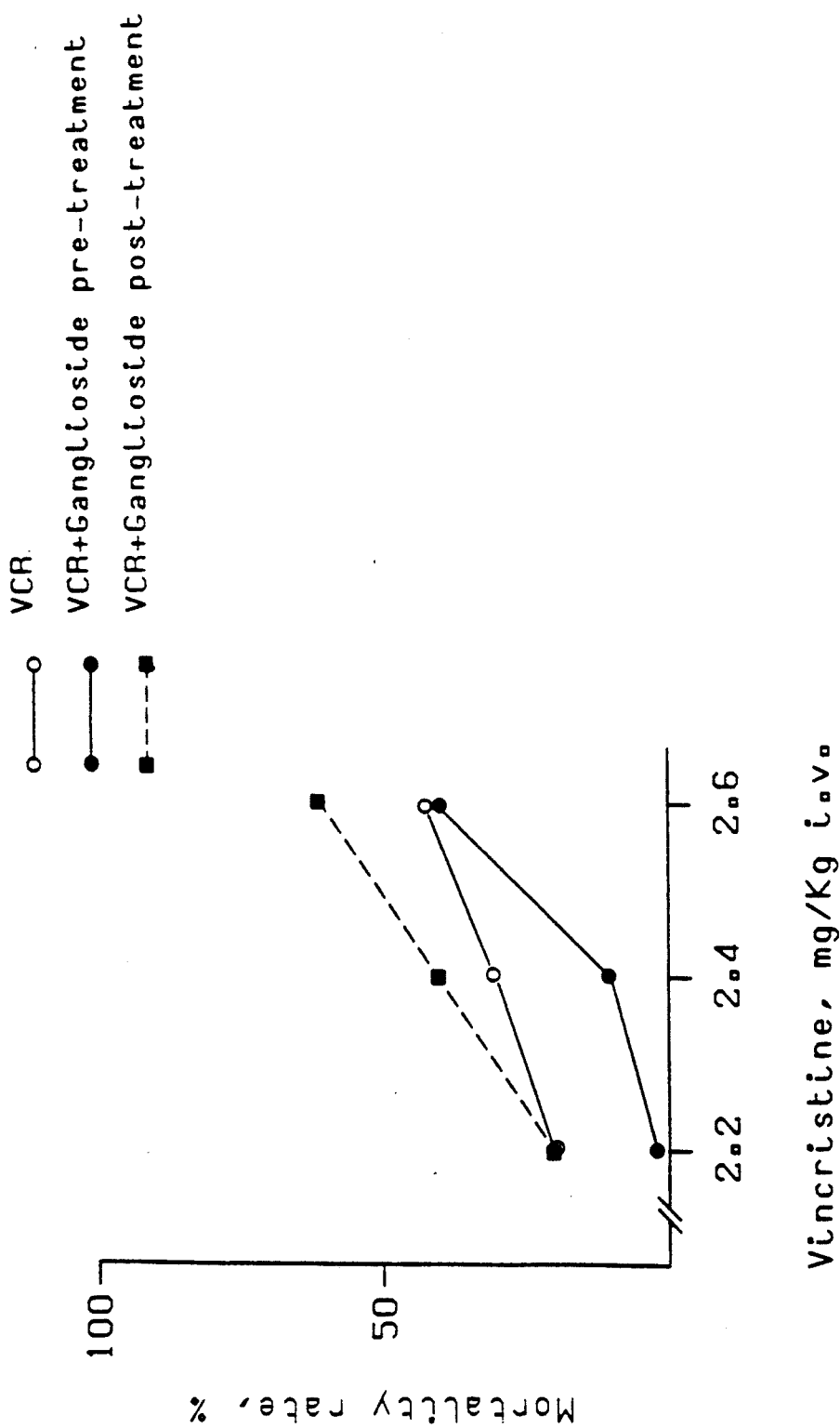
FIG.1 Effect of pre- and post-treatment with gangliosides on the toxicity induced by different doses of Vincristine (VCR). Ten mice in each group.

USE OF EXOGENOUS GANGLIOSIDES AS A PROTECTIVE FACTOR AGAINST TOXICITY BY ANTITUMOR DRUG VINCRISTINE

BACKGROUND AND SUMMARY OF THE INVENTION

The present invention concerns a specific composition comprised of a mixture of gangliosides and of its single fractions which have proved to have a protective effect in neurotoxicity caused by anti-blastics.

Gangliosides represent a family of complex glycolipid molecules, natural components of cellular membranes, and in particular of the neuronal membranes, involved in the processes of development, differentiation and neuronal regeneration.

Exogenous gangliosides are incorporated into the neuronal membranes in a stable manner (Toffano G. et al. (1980): J. Neurochem. 35, (4), 861–866; Aporti F. et al. (1981): Acta Oto-Laryingologica, 92. 433–437). This incorporation is associated with the activation of an enzymatic membrane system, (Na+, K+)ATPase, the activity of which is essential for nervous impulse conduction. Enzymatic incorporation and activation have been demonstrated both in vitro (Leon A. et al. (1981): J. Neurochem. 37, (2), 350–357) and in vivo (Aporti F. et al. (1981)).

Gangliosides are acid glycolipids belonging to the family of biological compounds known as glycosphingolipids. These comprise 4 basic structural units: one long aminoalcohol chain, one fatty acid, one oligosaccharide fraction and one or more sialic acid residues.

The long amino alcohol chain, present in cerebral gangliosides is identifiable as 4-sphingenine and its longest chain analogue as 4-eicosasphingenine; These compounds are commonly known as sphingosines.

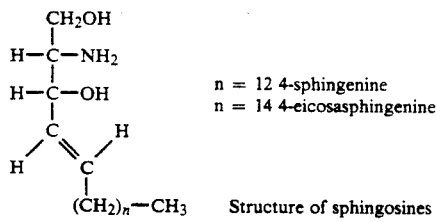

n = 12 4-sphingenine
n = 14 4-eicosasphingenine

Structure of sphingosines

The corresponding saturated compounds (sphinganines) are also present in gangliosides in smaller proportions.

A fatty acid is bound by an amidic bond to the basic sphingosine. In cerebral gangliosides this fatty acid is 95% stearic acid (18:0). Other fatty acids are found in smaller proportions, for example arachidic acid (20:0), palmitic acid (16:0) or palmitoleic acid (16:1$^9$). The amino alcohol and fatty acid together form a unit called a Ceramide, which represents the hydrophobic part of the ganglioside molecule.

The oligosaccharide chain bound to the ceramide characterizes the vaste family of glycosphingolipids to which gangliosides belong. Sphingolipids are classified in two subgroups, based on carbohydrates immediately bound to the ceramide. The first and smallest subgroup derives from galactosylceramide. Most glycosphingolipids, and therefore virtually all gangliosides, belong to the subgroup derived from glucosylceramide.

Sialic acid is present in cerebral gangliosides mainly in N-acetyl form, but the N-glycolyl form has been identified in some ganglioside species. This residue is generally known as neuraminic acid (NANA or NGNA).

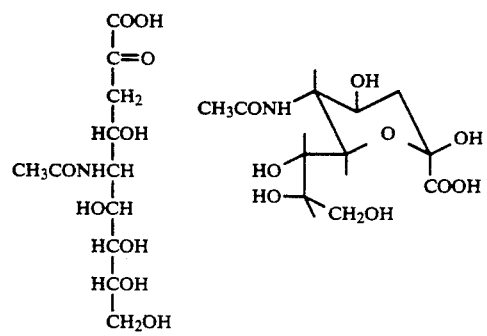

N-acetylneuraminic acid; open chain and hemiketal ring

The hydrophilicity of gangliosides is due to the oligosaccharide chain and to the number of sialic residues bound to this chain.

Distribution of Gangliosides

The highest concentration of gangliosides is found in cerebral grey matter, which contains about 2.5 micromoles of NANA per gram of wet matter (about 0.4% of the dry weight, 0.6% of the total lipids) (Ledeen R., Salsmar K., Cabrera M., J.Lipid Res.: 9, 129 (1968)). About 90% of the content of total gangliosides from mammal brains is formed by the four gangliosides with an identical oligosaccharide sequence:

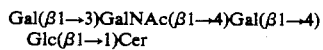

Gal($\beta$1→3)GalNAc($\beta$1→4)Gal($\beta$1→4) Glc($\beta$1→1)Cer

Most of the remaining 10% of the content of mammal cerebral gangliosides includes missing gangliosides of the terminal galactose or of the galactosyl-N-acetylgalactosamine unit (Svennerholm L., Mansson S., Li Y., J.Biol.Chem. 248. 740 (1973)).

Structure and Nomenclature of Gangliosides

Cerebral gangliosides were isolated and purified by ographic procedures. Firstly, the structure of the G$_{MI}$ ganglioside was determined. This structure was shown to be common to the four major gangliosides present in the mammal brain. The structure illustrated below refers to that described for G$_{MI}$ and is reported as an example. Table 1 contains descriptions of the four major mammal brain gangliosides.

STRUCTURE OF THE MONOSIALO GANGLIOSIDE GM1

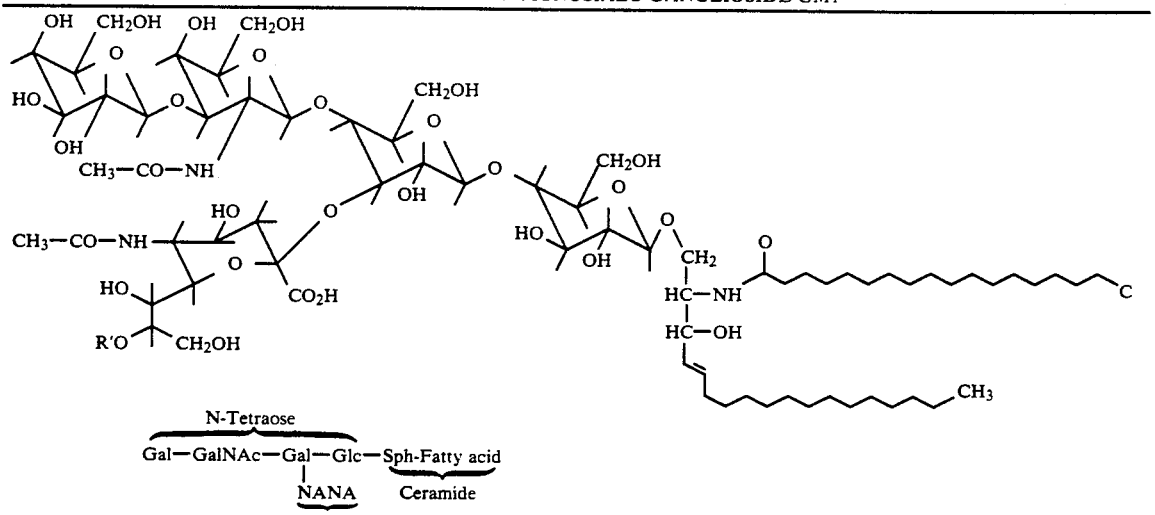

TABLE 1—Structures of the four major mammal brain gangliosides

| Symbol according to Svennerholm* | Abbreviation according to IUPAC—IUB | R | R' |
|---|---|---|---|
| $GM_1$ | $II^3$ —NeuAc—GgOse$_4$Cer | H | H |
| $GD_{1a}$ | $II^3$ —NeuAc—$IV^3$— —NeuAc—GgOse$_4$Cer | NANA | H |
| $GD_{1b}$ | $II^3$ —(NeuAc)$_2$GgOse$_4$Cer | H | NANA |
| $GT_{1b}$ | $II^3$ —(NeuAc)$_2$—$IV^3$— —NeuAc—GgOse$_4$Cer | NANA | NANA |

*(Svennerholm L., (1963): J. Neurochem. 10, 613)

OBJECT AND SUMMARY OF THE INVENTION

One object of the present invention is therefore to provide a method of treating and curing neurotoxicity due to antitumor agents with particular reference to the vinca alkaloids, producing a composition which is a mixture of gangliosides composed of $GM_1$, $GD_{1a}$, $GD_{1b}$ and $GT_{1b}$ in the following ratio expressed in percent:

$GM_1$—21%

$GD_{1a}$—40%

$GD_{1b}$—16%

$GT_{1b}$—19%

Another object of the present invention is to provide a pharmaceutical composition containing a mixture of gangliosides and their single fractions having a protective activity against neurotoxicity by antitumorals with particular reference to the alkaloid antiblastics of the vinca series. In particular this means a mixture of the gangliosides $GM_1$, $GD_{1a}$, $GD_{1b}$ and $GT_{1b}$ with the percentage composition reported previously. This composition possesses a protective activity against toxicity by antiblastics, useful in the cure and relief from the toxic side-effects of antitumor therapy with chemical substances.

A further object of the invention is to provide a medicament useful for the prophylaxis of general toxic effects or chronic neurotoxic effects caused by the administration of antineoplastic agents.

The invention also provides for the use of a mixture of gangliosides, particularly a mixture of gangliosides $GM_1$, $GD_{1a}$, $GD_{1b}$ and $Gl_{1b}$, for the manufacture of a medicament for the prevention or for the prophylactic treatment of general toxic effects or chronic neurotoxic effects caused by the subsequent administration of antineoplastic agents.

DETAILED DESCRIPTION OF THE INVENTION

As previously described, gangliosides represent a family of complex glycolipid molecules which are natural components of the cellular membranes. Given that gangliosides are mainly associated with neuronal membranes, it has been suggested (Fishman and coll. (1976): Science, 194 906-915) that they may play a part in the transfer of information through these membranes. Support for this hypothesis comes from a series of observations on events mediated by the cellular membranes in which these molecules are involved and which include: neuronal development (Dimpfel W. and coll.: In "Gangliosides in Neurological and Neuromuscular Function, Development and Repair", Rapport and Gorio, Raven Press 119-134, 1981), differentiation (Leon A. and coll.: In "Membranes in Growth & Development", Hoffman and coll., 311-320 1981) and regeneration (Gorio A. and coll. (1981a): In "Gangliosides in Neurological and Neuromuscular Function, Development and Repair", Rapport and Gorio, Raven Press 177-195).

A mixture of the gangliosides $GM_1$, $GD_{1a}$, $GD_{1b}$ and $GT_{1b}$, purified for parenteral use, has proved active in stimulating reinnervation due to increased neuronal growth (Gorio A. and coll. (1980): Brain Res. 197, 236-241). The activity which promotes nervous neuronal growth has been confirmed both in models of neuronal tissue culture in vitro (Roisen F. J. and coll. (1981): Science, 214, 577-578; Hauw J. J. and coll. (1981): Neurophysio- logie. C. R. Acad. Sc. Paris, 292, (8), 569-571)) and in models of animal denervation in vivo (Gorio and coll, "Brain Res. 197, 236-241), Gorio A.

and coll. (1981): In "Nervous system regeneration. Birth Defects; original article series", 19, (4), 157-174, (1983), Haber B. and coll.

The animal models in vivo (denervation of rat fast twitch muscle by crushing of the sciatic nerve, partial denervation of the soleus muscle of rat by resection and dislocation of the nerve root L5) gave both electrophysiological and morphological evidence of increased collateral nerve growth after treatment with exogenous gangliosides (5-50 mg/Kg per day for parenteral injections), resulting in faster functional recovery.

Functional electrophysiological evidence of faster healing of the lesioned nerve, due to treatment with gangliosides, has been demonstrated in various animal models, including sensory nervous function after cutting of the nerve (Norido F. and coll. (1981): Experientia, 37, 301-302); decrease in cochlear function following noise (Aporti F. and coll. (1977): Nuovo Arch. Otol. Rinol. Laringol. 5, (1), 25-32); diabetic neuropathies in genetically diabetic mice (Norido F. et coll., Muscle & Nerve, 5, 107-110 (1982); neurotoxin poisoning, (Aporti F. and coll. (1981): Acta Otolaryngologica 92, 433-437, (1981); Maroni M. and coll. Clinical Toxicology 18, (12) 1475-1484 (1981).

On the basis on these experimental data the mixture of gangliosides $GM_1$, $GD_{1a}$, $GD_{1b}$ and $GT_{1b}$ is considered therapeutically useful in a wide range of complaints affecting the peripheral nervous system where reinnervation can be stimulated and speeded up.

Furthermore, this mixture of gangliosides has proved useful for its protective activity in neurotoxicity by antiblastics in general, with particular reference to the alkaloids derived from the vinca series. This result represents the object of the present invention.

Introductive Information on Gangliosides and the Oncogenic Phenomenon

As discussed above, gangliosides are ubiquitous membrane components, the majority of which are present in the outer leaflet of the lipid layer of the plasma membrane (Ledeen R. (1984): TINS 8, 169-174).

It is well known from literature that gangliosides are involved in regulation phenomena and cellular recognition; it has therefore been verified that they play a role in development and cellular differentiation. Furthermore it is known that the oncogenic phenomenon is associated with important changes in the cell surface of glycosphingolipids (including, therefore, gangliosides). On this basis it has been postulated that gangliosides may play a role (as yet not well defined) in growth regulation, differentiation and cell interaction (Hakomori S. (1981): Ann. Rev. Biochem. 50, 733-764).

Indeed, in embryonic and histogenic development and differentiation, the cellular interactions are mediated by a continuous change of cell surface molecules encoded by a genetic program. During this process, there occur remarkable phase-dependent changes in cell surface ganglioside content and complexity.

Some examples of this phenomenon are:
a) expression of tetanus toxin (Koulakoff A. et al. (1983): Develop. Biol. 100, 350-357) and cholera toxin (Willinger M. and Schachner M. (1980): Develop. Biol. 74, 101-117) binding sites in CNS occurs only on postmitotic neurons;
b) in the intestinal epithelium, the undifferentiated cells are characterized by the presence of Lac-Cer, Glu-Cer and absence of $GM_3$, while the differentiated cells are characterized by high levels of $GM_3$ (Ledeen R. (1984 TINS 8, 169-174);
c) there is a remarkable increase in $GM_{1b}$ when the amyloid cells are induced to differentiate in macrophages (Ledeen R. (1984 TINS 8, 169-174).

These and other examples which are not mentioned here, such as modifications of gangliosides during cell-cell contact, suggest that the expression of specific gangliosides on the cell surface is correlated with the switch of cellular programs from the proliferative to the non-proliferative state (Koulakoff A. et al. (1983): Develop. Biol. 100, 350-357). Furthermore, their expression may define cell-cell interaction, cell migration and cell differentiation.

Support for the latter derives from in vitro experiments, conducted by the addition of exogenous gangliosides to proliferating (e.g. 3T3, neuroblastoma, glioma, etc.) or non-proliferating cells (e.g. primary neurons) in culture. In all cases the exogenously added gangliosides enhance cellular differentiation. In the case of proliferating cells, this effect is associated with decreased proliferation (see below) (Haber B. and Gorio A. eds (1984): J. Neurosci. Res.).

A possible role for gangliosides in the regulation of cell growth has been suggested by the following:
a) synthesis of specific gangliosides is greatly enhanced in association with "contact inhibition" of cell growth (Ledeen R. (1984 TINS 8, 169-174);
b) ganglioside synthesis increases when cell growth is arrested or induced in transformed cells by differentiating agents (Ledeen R. (1984 TINS 8, 169-174);
c) exogenous addition of gangliosides, including $GM_1$, incorporated into plasma membranes inhibits cell growth and induces contact inhibition. This effect has been observed in a number of cell lines (i.e. 3T3, neuroblastoma, glioma) (Haber B. and Gorio A. eds (1984): J. Neurosci. Res.; Ledeen R. et al. eds (1984): Adv. Exper. Med. and Biol. 174).

Hence, ganglioside synthesis increases when proliferation is arrested. Furthermore, exogenous supplementation of gangliosides is capable of arresting or delaying cell proliferation. It is worth noting that this latter effect is not in any way associated with cytotoxicity.

Changes in ganglioside patterns of the cell surface have been observed in various types of tumoral cells and as a specific response to different transforming carcinogenic agents and therefore can be considered a common phenomenon usually associated with transformation (Hakomori S. (1975): Biochim. Biophys. Acta 417, 55-89.

During oncogenic transformation, three categories of changes essentially occur in cell surface glycolipids, including gangliosides: incomplete synthesis, neosynthesis and organizational membrane rearrangements of the glycolipid molecules (Hakomori S. (1984): TIBS 10, 453-458). Both the precursor which accumulates due to incomplete synthesis, and the neoglycolipid formed by neosynthesis (usually minor glycolipids or gangliosides), are held to be a "tumor-associated" antigenic expression when it is not detectable on the progenitor cell surface. Furthermore, these tumor-associated antigens are sometimes characterized as having an unusual ceramide composition.

Basic Information for the Association of Gangliosides-Vincristine (VCR) for the Treatment of Tumoral Diseases Vincristine is a widely used antineoplastic agent and is successfully used in the treatment of leukaemia, lymphoma and in general in advanced forms of cancer (Holland J. F. et al. (1983): Cancer Res., 33, 1258-1264). The major drawback to extensive use of vincristine in the various tumoral pathologies is its high degree of toxicity and in particular one of the main side effects is the onset of signs of peripheral and autonomic neurotoxicity.

The neuropathy appears typically as loss of tendon reflexes, paraesthesias, muscle pain and weakness, constipation and abdominal pain. This neurotoxicity places severe limitations on the application of the doses and administrations necessary to cure tumoral pathologies and often leads to discontinuation of the drug (Arnold A.M. et al. (1985): The Lancet, Feb. 9th).

The mechanism of antimitotic action of vinca alkaloids consists in an interference with microtubule assembly in the mitotic spindle. This microtubule-disrupting effect is thought to be responsible also for morphological alterations of axons and neurons in experimental animals, showing focal axonal swellings, disorganized accumulations of neurofilaments (Cho E. S. et al. (1983): Arch. Toxicol. 52, 83-90) and microtubular crystalloid inclusions in neurons (Sato M., Miyoshi K. (1984): Acta Neuropathol. 63, 150-159). From an electrophysiological point of view, the studies in man by McLeod and Penny (J. Neurol. Neurosurg. Psychiat. 32, 297-304, 1969) and Guiheneuc et al. (J. Neurol. Sci. 45, 355-366, 1980) indicated that VCR-induced neuropathy was of a dying-back type, involving distal, retrograde axonal degeneration. These distal degeneration processes cause partial denervation of the target muscle. In this situation reparative sequences in the form of collateral sprouting phenomena by viable axons appear to represent the organism's attempt to reinnervate the targets abandoned by dwindling axons (Brown M. C. et al. (1981): Ann. Rev. Neurosci. 4, 17-42).

McLeod and Penny (1969) found that, after interruption of VCR therapy, these physiological repair processes regain efficiency and permit rapid regeneration of the nerve fibres. It is on the other hand well known that parenteral administration of ganglioside mixture (trademark CRONASSIAL) in experimental animals stimulates repair processes in the peripheral nerve by a mechanism based on facilitation of nerve sprouting (Gorio A. et al. (1980): Brain Res. 197, 236-241). The extensive clinical research carried out has shown that the ganglioside mixture drug Cronassial$^R$ is therapeutically advisable in a large variety of peripheral nervous system disorders, where stimulation of reparative innervation represents a clinical advantage. Such peripheral neuropathies include some toxic forms such as iatrogenic neuropathies caused by vinca alkaloids used for treatment of neoplasia.

In the specific field of Vincristine induced neuropathy, Dantona et al. (1978): Rivista Scientifica ed Educazione Permanente, (Suppl. 9), 155-158), described a series of 40 patients with acute neurotoxic syndromes induced by vincristine. These patients received 20 mg of the ganglioside mixture CRONASSIAL$^R$ daily for 20 days, followed by 10 mg daily for more than 10 days. The patients were regularly interviewed, paying particular attention to their symptoms and 57.5% of the patients reported a significant degree of subjective improvement. The paresthesia symptom in particular was found to subside as early as the fourth day after start of therapy. This uncontrolled exploratory experiment was followed by a controlled trial in a smaller number of patients.

Azzoni (Il Policlinico, Sez. Medica, 85, (4), 255-262 (1978)) studied seven ganglioside CRONASSIAL$^R$-treated patients against seven untreated comparable patients in parallel. The treated patients received 20 mg of ganglioside mixture CRONASSIAL$^R$ i.m. daily for 4-6 weeks, concurrently with Vincristine administration for underlying neoplastic disorders. The effect of treatment was monitored in symptom scoring for four major neurological alterations: paresthesia, ankly jerk areflexia, force of foot dorsiflexion and bowel dysfunction. The symptom scores after the treatment cycle were analyzed by means of the Armitage sequential analysis, in view of the low number of patients. This analysis showed that CRONASSIAL$^R$ therapy, at the dosage level tried, was effective in preventing the occurence of moderate neurotoxic signs (paresthesia and loss of ankle jerk reflex).

Experimental Studies for the Present Invention

In order to exclude the possibilities of a physical-chemical or biological interaction between the gangliosides contained in the ganglioside mixture CRONASSIAL$^R$ and Vincristine, and to investigate the possibility that the antitumoral activity of Vincristine may be impaired by concomitant administration of the ganglioside CRONASSIAL$^R$, various experiments were conducted in animals with concurrent administration of Vincristine and gangliosides. In particular:

1. acute and chronic toxicity
2. antitumoral effect

1. Effect of Gangliosides on Acute Vincristine Toxicity

Materials and Methods

Animals

The mice were subdivided into groups of not more than 8 in standard cages. Food and water were provided ad lib. The animals were housed in rooms under strictly controlled conditions.

Drugs 1 mg of Vincristine was diluted to obtain the concentration necessary to inject 0.1 ml/10 g. body weight.

A solution of gangliosides was prepared by addition of sterile distilled water in a quantity sufficient to obtain a final concentration of 200 mg/kg in a volume of 0.2 ml. This dose was administrated to mice weighing about 20g.

Results

The results are reported in Table 2, from which it can be seen that the ganglioside mixture does not protect against acute toxicity from single i.v. doses of Vincristine.

TABLE 2

Acute lethality by Vincristine and Vincristine + gangliosides in mouse
Aim: Reduction in toxicity of antitumoral drugs

| | Dosage mg/kg | Route/ Time | No. Survivors at 30 days | % Survivors at 30 days |
|---|---|---|---|---|
| Vincristine | 3.0 | e.v. | 2/8 | 25 |
| Vincristine + | 3.0 | e.v. | 1 | 12.5 |

TABLE 2-continued

Acute lethality by Vincristine and
Vincristine + gangliosides in mouse
Aim: Reduction in toxicity of antitumoral drugs

| | Dosage mg/kg | Route/ Time | No. Survivors at 30 days | % Survivors at 30 days |
|---|---|---|---|---|
| Gangliosides | 200 | i.p. 6 hrs before VCR | | |

2. Effect of Ganglioside Treatment on Chronic Vincristine Toxicity

Materials and Methods

Male mice CD-1 (ICR) BR (Charles River, Italy) weighing 25-30 g were used for the whole experiment. The animals were housed in groups of 10 per cage and fed with standard laboratory chow and tap water ad libitum. The animals were housed at constant room temperature (21°±1° C.) and relative humidity (60%) with controlled cycles of light/dark (light from 8.00 a.m. to 8.00 p.m.).

Vincristine sulphate (Lilly) was dissolved in saline and injected i.v. in a dose volume of 10 ml/kg, whereas the gangliosides were solubilized in a phosphate buffer (0.01M; pH 7.5) containing 0.8% of NaCl and administered i.m. at a dose volume of 5 ml/kg.

Pre-treatment with Gangliosides

The ganglioside mixture (or vehicle) was administered i.m. daily for 5 consecutive days at different doses (50, 100 and 200 mg/kg) and Vincristine was injected i.v. 5 hours after the last treatment with gangliosides (or vehicle) in doses of 2.4 and 2.6 mg/kg.

Post-treatment with Gangliosides

The ganglioside mixture (or vehicle) was administered i.m. in doses of 200 mg/kg 5 hours before i.v. treatment with Vincristine for 5 consecutive days
The doses of Vincristine were of 2.2, 2.4 and 2.6 mg/kg.

The mortality rate was estimated by the number of animals that died within the first 14 days of Vincristine treatment.

The statistical significance between mortality rates was assessed by means of Fisher's exact probability test.

Results

The results of the tests are reported in Tables 3 and 4 and graphed in FIG. 1. On the basis of the mortality rate curve after administration of Vincristine, doses between 2 and 3 mg/kg were chosen for the investigation with gangliosides. The first experiment compared the effects of ganglioside treatment before and after Vincristine injection.

In the case of post-treatment, a single administration of gangliosides was given in order to exclude the possibility that the greater efficacy of pre-treatment with gangliosides in reducing Vincristine toxicity, might only be due to the last ganglioside injection.

As reported in FIG. 1 a reduction in Vincristine toxicity was observed when the ganglioside mixture was administered subchronically before but not after Vincristine injection. This effect was obtained using the maximum dose of gangliosides (200 mg/kg). When lower doses of ganglioside mixture were administered, it was possible to notice a dose-dependent effect of the protective action of gangliosides (Table 3), with the exception of the abnormal mortality rate of the group treated with gangliosides 100 mg/kg and Vincristine 2.6 mg/kg.

Further experiments were carried out with doses of 200 mg/kg of gangliosides. The relative data can be seen in Table 4.

TABLE 3

Effect of sub-chronic pre-treatment with different doses of gangliosides on acute lethal Vincristine (VCR) toxicity

| Treatment | Mortality rate |
|---|---|
| Vehicle + VCR 2.4 mg/kg i.v. | 7/10 |
| Gangliosides 50 mg/kg i.m + VCR 2.4 mg/kg i.v. | 2/10 |
| Gangliosides 100 mg/kg i.m + VCR 2.4 mg/kg i.v. | 1/10 |
| Gangliosides 200 mg/kg i.m + VCR 2.4 mg/kg i.v. | 0/10 |
| Vehicle + VCR 2.6 mg/kg i.v. | 5/10 |
| Gangliosides 50 mg/kg i.m + VCR 2.6 mg/kg i.v. | 4/10 |
| Gangliosides 100 mg/kg i.m + VCR 2.6 mg/kg i.v. | 9/10 |
| Gangliosides 200 mg/kg i.m + VCR 2.6 mg/kg i.v. | 2/10 |

TABLE 4

Effect of subchronic pre-treatment with gangliosides (200 mg/kg) i.m.) on acute lethal Vincristine (VCR) toxicity.

| Treatment | Mortality rate | |
|---|---|---|
| | No. | % |
| Subchronic vehicle + VCR 2.4 mg/kg i.v. | 19/50 | 38 |
| Subchronic gangliosides + VCR 2.4 mg/kg i.v. | 3/50* | 6 |
| Subchronic vehicle + VCR 2.6 mg/kg i.v. | 30/50 | 60 |
| Subchronic gangliosides + VCR 2.6 mg/kg i.v. | 17/50* | 34 |

*P 0.01 vs. suitable controls (Fischer's exact probability test)

Antitumoral Effect of Vincristine in Association with Gangliosides

Materials and Methods

The following strains were used for the various tumors:
Male Swiss Schneider mice weighing 27 g. were used for experiments on sarcoma S180.
Female $C_{57}B1$ mice weighing 20 g. were used for experiments on melanoma B16.
Male $BDF_1$ mice weighing 30 g. were used for experiments on leukemia L1210.
$C_{57}Bl$ mice weighing 20 g. were used for experiments on Lewis lung.

Tumors

Sarcoma S180

This tumor has been transplanted into the same strain of mouse in this laboratory for over 10 years. The transplant was carried out by s.c.inoculation of 0.1 ml of a tumoral homogenate obtained by finely mincing viable tumoral tissue, passed repeatedly through a 26 gauge needle into a sterile Petri dish. 0.1 ml of Penicillin (20,000 u/ml) and streptomycin (20,000 u/ml) were added to the solution. 5 mg of Neomycin were also added.

Melanoma B16

This tumor was prepared by inoculation in the same way as that used for sarcoma S180.

L1210

Spleens were removed from the animals 7 days after inoculation of L1210 cells and were then finely minced with isotonic saline 1:100. 0.1 ml of this spleen and leukemia L1210 cell suspension was then injected s.c. into the flank of each BDF$_1$ mouse.

Lewis Lung (3LL)

This tumor was prepared by inoculation in the same way as that used for sarcoma S180.

Drugs

Vincristine

A standard vial containing 1 mg of Vincristine was used. It was prepared with a suitable volume of diluting solution to give the final concentration required for injection into 0.1 ml/10 g. of body weight.

Cronassial

A solution of this substance, which is a mixture of four gangliosides, was prepared by adding a volume of sterile distilled water suffi- cient to give a concentration of 200 mg/kg in a volume of 0.2 ml. This dose is administered to mice weighing approximately 20 g.

Results

The results of these studies are reported in Table 5.

TABLE 5

| | | | Antitumoral activity with and without CRONASSIAL | | | | |
|---|---|---|---|---|---|---|---|
| Tumor | Host | Drug | Dose mg/kg | Days | Route | Time | |
| | | | | | | | Mean tumor weight (g) |
| S180 | SN | VCR | 0,5 | 1-6 | i.p. | | 0,64 |
| S180 | SN | VCR } CRON | 0,5 200 | 1-6 1-6 | i.p. i.p. | 6 hours before VCR | 0,69 |
| S180 | SN | Controls CMC | | | | | 1,05 |
| B16 | C57B1 | VCR | 0,5 | 1-4, 7-11 | i.p. | | 1,46 |
| B16 | C57B1 | VCR } CRON | 0,5 200 | 1-4, 7-11 1-4, 7-11 | i.p. i.p. | 6 hours before VCR | 1,66 |
| B16 | C57B1 | Controls CMC | | | | | 2,33 |
| | | | | | | | Mean survival time (gg.) |
| L1210 | BDF1 | VCR | 1,0 | 1-3 | i.p. | | 7,8 |
| L1210 | BDF1 | VCR } CRON | 1,0 200 | 1-3 1-3 | i.p. i.p. | 6 hours before VCR | 10,3 |
| L1210 | BDF1 | Controls CMC | | | | | 8,0 |

Vincristine, with and without the ganglioside mixture CRONASSIAL$^R$, tested in tumors S180, B16 and L1210, showed that the ganglioside mixture CRONASSIAL$^R$ does not interfere with any antitumor activity that Vincristine may have, as shown by the inhibition of tumor growth in the average in the average survival time.

On the contrary, the results obtained with leukemia L1210 show that the mortality caused by toxicity by Vincristine alone may be reduced (if administered with the ganglioside mixture CRONASSIAL$^R$ and that the effectiveness of Vincristine against L1210 is enhanced, with an average survival time of 10.3 days, compared with 7.8 days for Vincristine alone. This difference is statistically significant.

Pharmaceutical Composition

For the new therapeutic application according to the invention, the ganglioside formulation should contain the individual gangliosides in the following proportions:

| Individual gangliosides | percentage of weight |
|---|---|
| GM$_1$ | from 19 to 23 |
| GD$_{1a}$ | from 36 to 44 |
| GD$_{1b}$ | from 14 to 18 |
| GT$_{1b}$ | from 17 to 21 |

In one particular, preferential formulation the individual gangliosides are combined together in the following proportions of weight:

GM$_1$—21%

GD$_{1a}$—40%

GD$_{1b}$—16%

GT$_{1b}$—19%

To prepare a pharmaceutical composition according to the invention, the formulation should preferably contain a titer of total gangliosides (GM$_1$+GD$_{1a}$+GD$_{1b}$+GT$_{1b}$) of 95.0% (calculated with reference to dry weight). The preparations may be solutions of ganglioside compounds or freeze-dried powders of the compound in association with one or more pharmaceutically acceptable vehicles or diluents, containing a phosphate medium with a suitable pH and isosmotic with physiological fluids. Each dose of the composition should contain between 10 and 100 mg of the ganglioside mixture.

The particular dosage depends on the effect desired and on the administration route. For example the dosage may be between 1.43 and 0.143 mg of active compound per kilo of body weight per day at standard dosage of between 100 and 10 mg. Some possible pharmaceutical compositions may be the following:

Preparation No. 1

Each 2 ml vial contains:

| ganglioside mixture in the proportions: | 100 mg |
|---|---|
| GM$_1$ 21% | |
| GD$_{1a}$ 40% | |
| GD$_{1b}$ 16% | |
| GT$_{1b}$ 19% | |
| phosphate buffer pH 7.6M/100 in | 2 ml |
| apyrogenic, sterile, distilled water q.s.a. | |

Preparation No. 2

Each 2 ml vial contains:

| ganglioside mixture in the proportions: | 10 mg |
|---|---|
| GM$_1$ 21% | |
| GD$_{1a}$ 40% | |
| GD$_{1b}$ 16% | |
| GT$_{1b}$ 19% | |
| phosphate buffer pH 7.6M/100 in | 2 ml |
| apyrogenic, sterile. distilled water q.s.a. | |

Preparation No. 3

Each 2 ml vial contains:

| ganglioside mixture in the proportions: | 25 mg |
|---|---|
| GM$_1$ 21% | |
| GD$_{1a}$ 40% | |
| GD$_{1b}$ 16% | |
| GT$_{1b}$ 19% | |
| phosphate buffer pH 7.6M/100 in | 2 ml |
| apyrogenic, sterile, distilled water q.s.a. | |

Preparation No. 4

Each freeze-dried vial contains:

| ganglioside mixture in the proportions: | 75 mg |
|---|---|
| GM$_1$ 21% | |
| GD$_{1a}$ 40% | |
| GD$_{1b}$ 16% | |
| GT$_{1b}$ 19% | |

One 2 ml vial of solvent contains:

| mannitol | 25 mg |
|---|---|
| phosphate buffer pH 7.6M/100 in | 2 ml |
| apyrogenic, sterile, distilled water q.s.a. | |

General Conclusions and Uses in Therapy

The results presented on the prevention of chronic Vincristine toxicity by concurrent administration of a ganglioside mixture were surprising, since it is not possible to associate this general protective effect with the neuronal reparative effect of gangliosides alone, observed in earlier research. Indeed, on the basis of previous results obtained with gangliosides, it was hypothesized that gangliosides may prevent Vincristine neuropathy and not those neuropathies caused by chronic toxicity of a more general character.

The three areas most affected by Vincristine are the hematologic system, the gastrointestinal system and the nervous system. On the other hand it is difficult to explain the protective effect of gangliosides, when this is considered only as an effect on the central or autonomic nervous systems, since the mortality dertermined in the animals by Vincristine cannot be attributed only to its effects on the peripheral or autonomic nervous systems. This implies, therefore, that gangliosides act by means of an action mechanism of a more general nature and different from that hypothesized by previous studies.

Furthermore, the effect could be reproduced with other antitumor drugs, such as mitozantrone, cys-platinum, methotrexate, adriamycin, daunomicin and cyclophosphamide, in which there is a high degree of toxicity both general and neuronal. It is important to note that gangliosides do not interfere negatively with the antitumoral activity of Vincristine, and in the case of experimental leukemia there would appear to be positive efficacy of the drug.

Considering its use in therapy it is essential to observe that:

the exogenous addition of gangliosides with cell lines in transformation, decreases or slows down cell proliferation and favours cell differentiation the effect of gangliosides is not cytotoxic and is reversible the antiproliferative effect of gangliosides may depend on the cell type and perhaps on the considered cell's dependence on growth factor for proliferation.

Vincristine on the other hand inhibits cell proliferation independently of the type of cell and the growth factor considered. However, its effects are due to its cytotoxicity to both transformed and not transformed proliferating cells. As such, the association of ganglioside-VCR in tumoral diseases may be considered valid. Gangliosides may make it possible to use lower doses of VCR as an antitumoral drug, lessening as a result the cytotoxic effect of VCR on the normal cells. On the other hand it is well known that the administration of anti-tumoral drugs such as VCR in patients suffering from tumors causes serious side-effects. It is therefore very desirable to bring about a reduction in these side effects (which are due to a more general toxicity of the drugs).

In summary, the data obtained proved very different from those expected, since they do not lead back to the nervous system. They are, rather, quite indicative of a protective or prophylactic action against the side-effects of a general toxic nature caused by administration of antiblastics of the vinca series. This type of action makes it possible to prolong the period of treatment with Vincristine in doses high enough to slow down tumor growth and at the same time delay the onset of the above mentioned side-effects.

Administration of the ganglioside mixture, in particular the ganglioside mixture CRONASSIAL$^R$ mixture, provides for the prophylaxis of general toxic effects or chronic neurotoxic effects caused by the administration of antineoplastic agents including neurotoxic effects such as the loss of tendon reflexes, paresthesia, muscular pain, muscular weakness, constipation and abdominal pain. The prophylactic activity is particularly evident when the ganglioside mixture is administered prior to the administration of the antineoplastic agent, particularly subchronically, daily for five consecutive days before administration of the antineoplastic agent, and especially where the antineoplastic agent is administered about five hours after the last administration of the ganglioside mixture.

Having thus described the invention, it is obvious that there can be several variations of the same. These variations must not be considered outside the essential aim of the invention and all these modifications should be considered obvious by an expert of the art and should be included in the aims of the following claims.

I claim:

1. A method for protective or prophylactic action against chronic neurotoxic effects selected from the group consisting of the loss of tendon reflexes, paresthesia, muscular pain, muscular weakness, constipation and abdominal pain caused by the administration of vincristine which comprises the administration to a patient of about 200 mg/kg of a mixture of gangliosides which contains about 23% of $GM_1$, about 40% of $GD_{1a}$, about 16% of $GD_{1b}$ and about 19% of $GT_{1b}$ for at least five consecutive days prior to administration of vincristine, and said vincristine is administered within about 5 hours after the last administration of said ganglioside mixture.